United States Patent
Manghisi et al.

[11] 3,969,368
[45] July 13, 1976

[54] 2-SUBSTITUTED BENZODIOXOLES
[75] Inventors: Elso Manghisi, Monza; Aldo Salimbeni, Milan, both of Italy
[73] Assignee: Istituto Luso Farmaco d'Italia S.r.l., Milan, Italy
[22] Filed: Feb. 1, 1973
[21] Appl. No.: 328,633

[30] Foreign Application Priority Data
Feb. 9, 1972  Italy .................................. 20407/72
Dec. 4, 1972  Italy .................................. 32458/72

[52] U.S. Cl. .................... 260/340.5; 260/268 C; 260/293.58; 260/326.5 C; 260/465 F; 260/473 G; 260/520 C; 260/559 B; 424/248; 424/250; 424/267; 424/274; 424/282; 260/247.7 T
[51] Int. Cl.² ............... C07D 317/58; C07D 317/72
[58] Field of Search ................................ 260/340.5

[56] References Cited
FOREIGN PATENTS OR APPLICATIONS
978,906  6/1965  France .............................. 260/340.5

OTHER PUBLICATIONS
Rosnati et al., Chem. Abstr., vol. 72 (1970), Abstr. No. 121407h.
Gardner et al., Chem. Abstr., vol. 66 (1967), Abstr. No. 75987y.
Rosnati et al., (Gazz.), Gazz. Chim. Ital., 1970, 100(1), pp. 3–13.

*Primary Examiner*—James A. Patten
*Attorney, Agent, or Firm*—Flynn & Frishauf

[57]  ABSTRACT

2-Substituted benzodioxoles are useful as pharmaceuticals having e.g. anti-inflammatory, analgesic, antipyrretic, antitussive, C.N.S. depressant, local anaesthetic, antiarrythmic, antihistaminic action and hypolipidic action.

7 Claims, No Drawings

2-SUBSTITUTED BENZODIOXOLES

The present invention provides, as new compounds, the benzodioxoles of the formula:

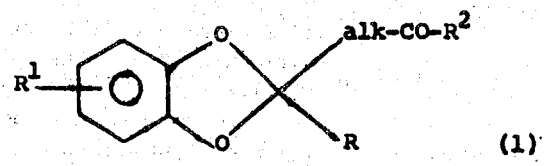

in which R represents hydrogen, lower alkyl, lower haloalkyl lower hydroxy-alkyl or an aryl or aralkyl residue unsubstituted or substituted by, in the aromatic ring, halogen or alkyl, or by hydroxyl or alkoxy; alk represents a lower, straight, branched, or cyclic, saturated or unsaturated alkyl group; and R and alk can be joined to form a spirane nucleus; $R^1$ represents hydrogen, halogen, lower alkyl, lower haloalkyl, hydroxy, nitro, amino, substituted amino, or a benzene ring condensed on the benzodioxole nucleus; and $R^2$ represents (a) a group —O—$R^3$ in which $R^3$ hydrogen, straight or branched alkyl, hydroxy-alkyl, aralkyl, aminoalkyl, or aminohydroxyalkyl; in which the amino group is unsubstituted or mono or disubstituted by lower alkyl or may form part of a heterocyclic ring (e.g. morpholine, pyrrolidine and the like); or (b) a group of formula:

in which $R^4$ and $R^5$, which can be the same or different each represent hydrogen, (linear, branched, or cyclic), lower alkyl hydroxyalkyl or aralkyl, aminoalkyl, in which the atom of nitrogen is unsubstituted, monosubstituted or disubstituted by alkyl or may form part of a heterocyclic ring, hydroxy, an acid group, or aryl unsubstituted or substituted by alkyl or halogen; or the group

represents the residue of an heterocyclic amine (e.g. pyrrolidine, morpholine, piperidine, piperazine, or N-substituted piperazine provided that when R = $CH_3$ and $R^1$ = H or 5—$CH_3$, the grouping —alk—CO—$R^2$ is different from carboxymethyl, 2-carboxyethyl, 1-methyl-2-carboxyethyl, 2-carboxypropyl, and the respective ethyl esters; when R = $CH_3$ and $R^1$ = 5—$NO_2$, the said grouping is different from carboxymethyl and the respective ethyl ester; when R = phenyl and $R^1$ = H, the said grouping is different from carboxymethyl and carbomethoxymethyl; and when R = H and $R^1$ = H the said grouping is different from —$CH_2$—$CONH_2$.

According to the invention, the aforesaid compounds are obtained by reaction between the appropriately substituted pyrocatechol and their ester derivatives with the carbonic or sulphuric acids and a ketone ester, a ketone amide or a ketone nitrile having the carbonyl function in beta, gamma and delta positions in relation to the other group in a linear branched or cyclic chain. Instead of the carbonyl compounds, the corresponding derivatives can be used, such as acetals with aliphatic alcohols, gem-dichloro- or di-bromo- compounds, enolic forms, or enamines.

As a condensing reagent, phosphoric anhydride is preferably used but other reagents can also be used, e.g. sulphuric, phosphoric, polyphosphoric, hydrochloric or trifluoroacetic acids, pyridine hydrochloride, calcium chloride, paratoluenesulphonic acid, ion exchange resins (such as Amberlite IRA 120), dicyclohexylcarbodiimide; or molecular sieve. The reaction temperature can vary between 0°–150°C. and the reaction is effected in the presence of at least one inert organic solvent, e.g. an aliphatic or aromatic hydrocarbon, a halogeno derivative thereof, an ether, ester or amide.

According to a variant of the process, the substituted pyrocatechol, or one of its reactive derivatives, is reacted with a dibromoester or a dibromoamide of the formula:

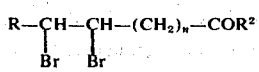

in which R and $R^2$ have the aforementined meanings, or with the corresponding nitrile.

In place of the dibromo derivative, a bromoolefine of the formula:

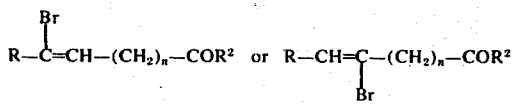

can also be used, especially where "n" = 0.

Preferably, the reaction is carried out in dimethylformamide in the presence of sodium hydroxide, at room temperature, but the dimethylformamide can be replaced by other solvents like the ones already described (and in addition, by ketones, such as methylethylketone and the like), and the sodium hydroxide by other basic catalysts, either organic or inorganic. If sodium methoxide is used, there forms together with the benzodioxole, also the benzodioxane isomer, which can be separated with suitable manipulation.

The benzodioxole ring can be obtained, according to another variant, by reaction of a pyrocatechol with an acetylene derivative of the formula:

in an anhydrous solvent belonging to the beforementioned classes, in presence of an organic or inorganic basic catalyst (e.g. tributylamine or potassium carbonate) at a temperature ranging from 0° to 100°C.

In the cyclization reaction intermediate compounds of the following formula can also be isolated:

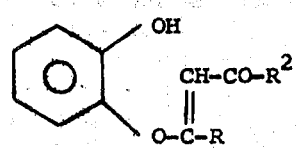

which, after being treated with alkaline agents (e.g. potassium carbonate) cyclize easily to give the corresponding benzodioxole.

In the cyclisation products obtained with the above methods, the residue $R^2$ can obviously be transformed by the common methods of organic chemistry, so as to have the other means ascribed to same in the general formula I.

One can thus obtain the acids ($R^2 = OH$) from the corresponding esters, amides and nitriles by acid or basic saponification; vice-versa, one can transform the acids into corresponding esters by using the common esterification methods which consist, for instance, in making the acid (or one of its metallic salts or a reactive derivative like another ester, a chloride, or a mixed anhydride reacting with an alcohol $R^3$—OH (in which $R^3$ has the beforementioned meaning) or with a relative derivative of the latter (e.g. an ester with a hydrohalic acid or p-toluenesulphonic acid) in the presence of at least one of the suitable catalysts which, according to the reaction, may be preferably an acid (e.g. hydrochloric acid, sulphuric acid, p-toluenesulphonic acid, or a Lewis-acid) or a base (where transesterifications are involved e.g. an alkali metal alkoxide, sodium hydroxide, or sodamide). Similarly, the benzodioxole acid (or one of its beforementioned reactive derivatives) can be converted into a corresponding amide by reaction with an amine of formula:

in which $R^4$ and $R^5$ have the meanings which have duly been described. In addition, there is a conversion of an acid into its higher homologues by Arndt-Eistert reaction, as in the case of formation of an acid by Grignard reaction between a halogen derivative of the formula

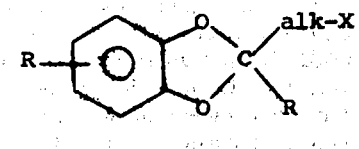

with magnesium and carbon dioxide.

The compounds of the general formula which contain one or more asymmetric atoms of carbon can be split into their stereoisomers by using the common separation methods.

From the compounds of the general formula 1, which contain a basic group, salts can be obtained with pharmaceutically acceptable inorganic acids, e.g. hydrochloric acid, hydrazoic acid, nitric acid, sulphuric acid, or phosphoric acid, and organic carboxylic acids, for instance propionic acid, glycolic acid, maleic acid, succinic acid, hydroxymaleic acid, fumaric acid, malic acid, tartaric acid, citric acid, glucuronic acid, benzoic acid, mandelic acid, salicylic acid, 4-aminosalicyclic acid, 2-phenoxybenzoic acid, 2-acetoxybenzoic acid, pamoic acid, nicotinic acid, and isonicotinic acid, and organic sulphonic acids, e.g. methanesulphonic acid, ethanesulphonic acid, 2-hydroxyethanesulphonic aci acid, ethane-1,2-disulphonic acid, p-toluenesulphonic acid, or naphthalene-2-sulphonic acid. Mono and poly salts are formed according to the number of salt-forming groups present in the molecules. Similarly, from the compounds of the formula 1, which contain an acid group, pharmaceutically acceptable salts can be obtained with metals (such as sodium, potassium, calcium, magnesium, and aluminium) or with organic bases (such as morpholine, pyrrolidine, ethanolamine, and N,N-dibenzylethylenediamine).

The benzodioxole derivatives of the invention have interesting pharmacological properties and, according to the substituents present, have anti-inflammatory, analgesic, antipyrretic, antitussive, C.N.S. depressant, local anaesthetic, antiarrythmic and antihistaminic action. Some of the compounds also have a hypolipidic action.

The new compounds can be administered topically, orally, or by injection as suitable pharmaceutical formulations in solid, liquid and suspension form e.g. as ointments, lotions, tablets, capsules, phials or syrups.

The tables that follow summarise the pharmacological characteristics of specific compounds described in this application, which are denoted by the following numbers:

LR 272 : (2-phenyl-1,3-benzodioxol-2-yl)acetic acid

LR 273 : (2-methyl-1 1,3-benzodioxol-2-yl)acetic acid

LR 289 : N-(N',N'-diethylaminoethyl)-2-(2-phenyl-1,3-benzodioxol-2-yl)acetamide hydrochloride.

LR 290 : N-(N',N'-diethylaminoethyl)-2-(2-methyl-1,3-benzodioxol-2-yl)acetamide citrate.

LR 292 : N,N-diethylaminoethyl(2-methyl-1,3-benzodioxol-2-yl)acetate citrate.

LR 293 : N,N-diethylaminoethoxyethyl-(2-methyl-1,3-benzodioxol-2-yl)acetate citrate.

LR 295 : N-morpholinoethyl-(2-phenyl-1,3-benzodioxol-2-yl)-acetate maleate.

LR 296 : N-morpholinoethyl-(2-methyl-1,3-benzodioxol-2-yl)-acetate.

LR 310 : (2-phenyl-1,3-benzodioxol-2-yl)acetamide.

LR 347 : N-(tert-butyl)-2-(2-phenyl-1,3-benzodioxol-2-yl)-acetamide.

LR 356 : N,N-dimethyl-2-(2-phenyl-1,3-benzodioxol-2-yl)-acetamide.

LR 411 : Ethyl(2-phenyl-5-chloro-1,3-benzodioxol-2-yl)-acetate.

LR 444 : (2-phenyl-1,3-benzodioxol-2-yl)acetohydroxamic acid.

LR 445 : N-(N',N'-diethylaminoethyl)-spiro-[1,3-benzodioxol-2,1''-cyclohexane]-2'-carboxyamide citrate.

LR 449 : N-benzyl-2-(2-methyl-1,3-benzodioxol-2-yl)-acetamide.

LR 471 : N-(N',N'-diethylaminoethyl)-3-(2-methyl-1,3-benzodioxol-2-yl)-propionamide.

LR 492 : N-(N',N'-diethylaminoethyl)-2-(2-methyl-1,3-benzodioxol-2-yl)-propionamide citrate.

LR 493 : N-(N',N'-diethylaminoethyl)-2-(2,5-dimethyl-1,3-benzodioxol-2-yl)-acetamide citrate.

The tables also show data for some drugs for comparison (phenyl-butazone, dihydrocodeinone, quinidine).

| Compound | LD$_{50}$ rat mg/Kg. e.p. | Anti-inflammatory activity in the rat (carraghenin oedema) dose reducing inflammation by 15%-mg/kg.e.p. | Therapeutic Index | Analgesic activity (acetic acid-induced stretching) % of rats protected |
|---|---|---|---|---|
| LR 411 | >1000 | 200 | >5 | 32 |
| LR 290 | 490 | 50 | 9.8 | φ |
| LR 292 | 1000 | 150 | 6.7 | φ |
| LR 347 | >1000 | 150 | >6.7 | 30 |
| LR 356 | >1000 | 200 | >5.0 | 50 |
| LR 449 | 1000 | 200 | 5.0 | 30 |
| LR 471 | 150 | 50 | 3.0 | 20 |
| LR 444 | 150 | 50 | 3.0 | 20 |
| Phenylbutazone | 450 | 50 | 9.0 | 40 |

| Compond | LD$_{50}$ rat mg/kg. e.p. | Anti-tussive activity in the rate (NH$_3$ aerosol) ED$_{50}$ mg./kg. e.p. | Therapeutic index LD$_{50}$/ED$_{50}$ |
|---|---|---|---|
| LR 272 | 250 | 33 | 7.6 |
| LR 273 | 250 | 15 | 15.7 |
| LR 293 | 720 | 67 | 10.7 |
| LR 296 | >1000 | 86 | >11.6 |
| LR 289 | 90 | 14 | 6.4 |
| LR 310 | 940 | 88 | 10.7 |
| LR 347 | >1000 | 115 | >8.7 |
| LR 295 | 490 | 64 | 7.7 |
| Dihydrocodeinone | 100 | 4.0 | 25.0 |

| Compound | LD$_{50}$ rat mg./Kg. e.p. | Anti-arrythmic activity in the rat (CaCl$_2$ arrythmia) ED$_{50}$ mg./kg. e.v. | Therapeutic Index | Local anaesthetic activity in rats total ED$_{50}$ mg. i.d. |
|---|---|---|---|---|
| LR 293 | 720 | 1.7 | 423.5 | 0.35 |
| LR 292 | >1000 | 3.5 | >285.7 | φ |
| LR 290 | 490 | 3.6 | 136 | φ |
| LR 445 | 150 | 3.2 | 46.9 | φ |
| LR 492 | 250 | 6.3 | 39.7 | φ |
| LR 493 | 250 | 8 | 31.3 | φ |
| Quinidine | 150 | 4.8 | 31.3 | 0.9 |

The following Examples illustrate the invention. The melting and boiling points are not corrected. The identity of the substances and their purity are determined by elementary analyses of C, H and N (and the halogens when present), infra-red spectra, N.M.R. and U.V.

The products mentioned in this invention have not yet been described in literature, with the exception of:

a. 3-(2-methyl-1,3-benzodioxol-2-yl)propionic acid and the corresponding ethylester; 2-methyl-2-(2-methyl-1,3-benzodioxol-2-yl) propionic acid and the corresponding ethylester. (R.T. Arnold et al, J.A.C.S. 54, 1410 (1942);

b. (2-phenyl-1,3-benzodioxol-2-yl)acetonitrile; (1,3-benzodioxol-2-yl)acetonitrile; (1,3-benzodioxol-2-yl)-acetamide. V. Rosnati, Sannicolo, G. Pagani, Gazz. Chimm. Ital 98 1069 (1968).

For none of these compounds has any pharmacological activity been mentioned.

EXAMPLE 1

Ethyl(2-p-chlorophenyl-1,3-benzodioxol-2-yl)-acetate.

98.9 g of P$_2$O$_5$ is added to a mixture of 64 g of ethyl p-chlorobenzoylacetate and 90.4 g of pyrocatechol, heated at 80°C in portions over about ½ hour. After 15 minutes the heating is interrupted and 1000 cc of benzene are added. The organic phase is decanted. The latter is repeatedly washed first with NaHCO$_3$ and subsequently with H$_2$O until same is rendered neutral and finally dried with Na$_2$SO$_4$. The solvent is removed in vacuum and the residual oil fractionated, b.p. 150°–155°C (0.4 mm.Hg).

Similarly, one prepares:

ethyl (2-phenyl-1,3-benzodioxol-2-yl)acetate(b.p. 173°–176°C/1 mm).

ethyl(2-bromomethyl-1,3-benzodioxol-2-yl)acetate (b.p. 146°–150°C/0.4 mm).

ethyl spiro-(1,3-benzodioxol-2,1'-cyclohexane)-2'-acetate (b.p. 120°–124°C/0.3 mm).

ethyl(2-ethyl-1,3-benzodioxol-2-yl)acetate (b.p. 91°–92°C/0.4 mm).

ethyl 3-(2-p-chlorophenyl-1,3-benzodioxol-2-yl)-propionate (b.p. 200°–210°C/0.4 mm).

ethyl(2-methyl-4-methoxy-1,3-benzodioxol-2-yl)acetate (b.p. 95°–100°C/0.6 mm), starting from 3-methoxypyrocatechol and ethyl aceto-acetate.

ethyl(2-methyl-5-chloro-1,3-benzodioxol-2-yl)acetate (b.p. 130°–140°C/1.8 mm), starting from 4-chloropyrocatechol and ethyl aceto-acetate.

ethyl(2-methyl-1,3-naphthodioxol-2-yl)acetate (m.p. 61°–62°C from benzene-hexane) starting from 2,3-dihydroxynapththalene and ethyl aceto-acetate.

EXAMPLE 2

Ethyl(2-phenyl-1,3-benzodioxol-2-yl)acetate.

To a suspension of 15 g NaH (as a 50% suspension in mineral oil) in 200 cc of DMF 17.1 g of pyrocatechol in 90 cc of DMF is added with refrigeration. After ½h, a solution of ethyl dibromocinnamate (52.6 g in 90 cc of DMF) or of ethyl betabromocinnamate (40 g in 70 cc of DMF) is introduced with vigorous shaking and maintaining the temperature below 30°C. The mixture is kept for 12 hours to allow the reaction to complete. The solvent is removed under reduced pressure. The residue is taken up with water and extracted with ether. The separated organic phase is repeatedly washed with 10% NaOH and subsequently with $H_2O$ until neutral. It is dried over $Na_2SO_4$, and the dried product is evaporated and the residual oil fractionated. b.p. 173°–176°C/1 mm.

When sodium methoxide is used as a condensing medium, 2-carbethoxy-3-phenyl-1,4-benzodioxane (b.p. 160°–165°C/0.4 mm) is obtained as a by-product.

EXAMPLE 3

Ethyl(2-methyl-1,3-benzodioxol-2-yl)acetate.

A mixture of 22.2 g of ethyl 3-methyl-3-(o-hydroxyphenoxy) acrylate, 13.8 g of $K_2CO_3$ and 100 cc of anhydrous acetone is heated for 5 h. After it has been cooled, it is filtered and the solvent is eliminated under reduced pressure. The residue is treated as indicated in Example 2. The product is an oil b.p. 83°–86°C/0.3 mm.

EXAMPLE 4

Ethyl(2-phenyl-5-chloro-1,3-benzodioxol-2-yl)acetate.

78.5 g of anhydrous $K_2CO_3$ are added, in parts, to a solution of 40.5 g of ethyl phenylpropiolate and 43.5 g of chloropyrocatechol in 200 cc of anhydrous acetone. The mixture is heated for 15 h. It is subsequently filtered and the solvent eliminated at low pressure. The residue is treated as indicated in Example 2. The product has b.p. 150°–155°C/0.3 mm.

EXAMPLE 5

Ethyl(2-methyl-1,3-benzodioxol-2-yl)acetate.

13 g of ethyl acetoacetate and 13.6 g of pyrocatechol carbonate are heated until evolution of $CO_2$ ceases. The residue is distilled under reduced pressure, b.p. 83°–86°C/0.3 mm.

EXAMPLE 6

(2-phenyl-5-chloro-1,3-benzodioxol-2-yl) acetic acid.

A mixture of 32 g. of ethyl(2-phenyl-5-chloro-1,3-benzodioxol-2-yl)acetate, 200 cc. of 95% ethanol and 150 cc. of 4% NaOH is refluxed for 2 hours. The alcohol is then removed under vacuum and, after cooling, the mixture is acidified with dilute HCl. The precipitated solid is filtered off and recrystallised from benzene-hexane, m.p. 117°–119°C.

Similarly can be prepared:

(2-methyl-1,3-naphthodioxol-2-yl) acetic acid (m.p. 127°–128°C. from benzene).

3-(2-p-chlorophenyl-1,3-benzodioxol-2-yl) propionic acid (m.p. 100°–1°C. from benzene-hexane).

(2-methyl-1,3-benzodioxol-2-yl) acetic acid (m.p. 60°–61°C. from benzene).

(2-p-chlorophenyl-1,3-benzodioxol-2-yl) acetic acid (m.p. 162°–163°C. from benzene).

Spiro-(1,3-benzodioxol-2,1'-cyclohexane) acetic acid (m.p. 138°C. from benzene.

Spiro-(1,3-benzodioxol-2,1'-cyclohexane)-2'carboxylic acid (m.p. 92°–94°C. from hexane).

EXAMPLE 7

β-N-morpholinoethyl 2-(phenyl-1,3-benzodioxol-2-yl)acetate.

17.5 g of triethylamine is added to 44.7 g. of (2-phenyl-1,3-benzodioxol-2-yl) acetic acid, suspended in 200 cc. of $CHCl_3$. The mixture is cooled with ice and 19 g. of ethyl chlorocarbonate are added dropwise. After 15 minutes 22.9 g. N-β-hydroxyethylmorpholine are introduced in the mixture. After 2 hours, water is added, and the organic phase is separated and dried with $Na_2SO_4$.

The solvent is removed under vacuum, and the maleate is then obtained from the residual oil, m.p. 114°–115°C. (from isopropyl alcohol).

Similarly, the following can be prepared:

β-N-morpholinoethyl(2-methyl-1,3-benzodioxol-2-yl)acetate (oxalate, m.p. 141°–142°C. from isopropyl alcohol).

N-benzyl-2-(2-methyl-1,3-benzodioxol-2-yl)acetamide (m.p. 105°–106°C. from benzene).

N-benzyl-2-(2-phenyl-1,3-benzodioxol-2-yl)-acetamide (m.p. 102°–103°C. from benzene-hexane).

N-(N',N'-Diethylaminoethyl)-2-(2-methyl-5-nitro-1,3-benzodioxol-2-yl)acetamide (b.p. 230°–245°C./0.4 mm).

EXAMPLE 8

N,N-Diethylaminoethyl(2-methyl-1,3-benzodioxol-2-yl)-acetate.

To a suspension of 19.4 g. of (2-methyl-1,3-benzodioxol-2-yl)acetic acid in 100 cc. of anhydrous acetone, 10.6 g. of $Na_2CO_3$ and subsequently 13.5 g. of N,N-diethylaminoethyl chloride in 20 cc. of anhydrous acetone are added in portions. The mixture is refluxed for 4 hours. The sodium 116°–formed is filtered off and the solution is evaporated. The residual oil is converted into the citrate, m.p. 116°117°C. (from isopropyl alcohol).

The following can be similarly obtained:

N,N-Diethylaminoethyl(2-phenyl-1,3-benzodioxol-2-yl)-acetate (maleate, m.p. 119°–121°C., from isopropyl alcohol).

EXAMPLE 9

N,N-Diethylaminoethoxyethyl(2-phenyl-1,3-benzodioxol-2-yl)-acetate.

To a mixture of 14.2 g. of ethyl(2-phenyl-1,3-benzodioxol-2-yl)-acetate, 8.05 g. of 2-methylaminoethoxyethanol and 215 cc. of anhydrous heptane, heated to 100°C., is added in small portions a solution of sodium ethoxide (obtained from 0.165 g. of metallic sodium in 10 cc. of absolute ethanol). Heating is continued until the azeotropic ethanol-heptane mixture no longer distils. The product is subsequently evaporated, and the residue is taken up with water and extracted with ether. The organic phase is washed with water and dried with $Na_2SO_4$. The solvent is removed under vacuum and the citrate is prepared from the residual oil, m.p. 83°–84°C. (from isopropyl alcohol).

Similarly are prepared:

N,N-diethylaminoethoxyethyl(2-methyl-1,3-benzodioxol-2-yl)-acetate (citrate, m.p. 83°–84°C., from isopropyl alcohol); Morpholinoethoxyethyl(2-methyl-1,3-benzodioxol-2-yl)-acetate (oxalate, m.p. 108°–109°C. from isopropyl alcohol);

Morpholinoethoxyethyl(2-phenyl-1,3-benzodioxol-2-yl)-acetate (oxalate, m.p. 149°–150°C. from 95% alcohol).

EXAMPLE 10

N-(N',N'-Diethylaminoethy)-2-(2-methyl-1,3-benzodioxol-2-yl)-acetamide.

30 g. of methyl(2-methyl-1,3-benzodioxol-2-yl)-acetate are added to 52 g. of N,N-diethylethylenediamine mixed with 50 mg. of metallic sodium. The mixture is heated under nitrogen until methanol released by the reaction no longer distils (4 hours). The excess amine is removed under vacuum, and the residue is converted into the citrate, m.p. 127°–128°C. (from 95% alcohol).

The following can be similarly prepared:

N-(N',N'-diethylaminoethyl)-2-(2-phenyl-1,3-benzodioxol-2-yl)-acetamide (hydrochloride, m.p. 143°–144°C. from anhydrous alcohol);

N-(N',N'-diethylaminoethyl)spiro-(1,3-benzodioxol-2,1'-cyclohexane)-2'-carboxyamide (citrate, m.p. 149°–151°C. from 95% alcohol);

N-(N',N'-dimethylaminoethyl)-2-(2-methyl-1,3-benzodioxol-2-yl)-acetamide;

N-methyl-N'-(2-methyl-1,3-benzodioxol-2-yl-acetyl)-piperazine;

N-(N',N'-diethylaminoethyl)-3-(2-methyl-1,3-benzodioxol-2-yl)-propionamide (m.p. 42°–43°C.);

N-(N',N'-diethylaminoethyl)-2-(2,5-dimethyl-1,3-benzodioxol-2-yl)-acetamide (citrate, m.p. 124°–6°C. from isopropyl alcohol);

N-(N',N'-diethylaminoethyl)-2-(2-methyl-5-chloro-1,3-benzodioxol-2-yl)-acetamide;

N-(N',N'-diethylaminoethyl)-2-(2-methyl-4-methoxy-1,3-benzodioxol-2-yl)-acetamide;

N-(N',N'-diethylaminoethyl)-2-(2-methyl-1,3-benzodioxol-2-yl)- propionamide (citrate, m.p. 108°–110°C. from anhydrous alcohol).

EXAMPLE 11

(2-phenyl-1,3-benzodioxol-2-yl)-acetamide.

To 22 g. of (2-phenyl-1,3-benzodioxol-2-yl)-acetic acid in 300 cc. of anhydrous benzene, in the cold, 18.1 g. of $PCl_5$ are added. After leaving the mixture for 2 hours to allow the reaction to be completed a cold solution of $NH_3$ in anhydrous ether is added to the mixture, in drops and with shaking. After 12 hours, the mixture is poured onto ice. The organic phase is separated, washed with $H_2O$ until neutral, and finally dried with $Na_2SO_4$. The solvent is removed under vacuum and the residue is recrystallised from benzene, m.p. 114°–15°C.

The following can be prepared similarly:

N,N-Dimethyl-2-(2-phenyl-1,3-benzodioxol-2-yl)-acetamide (m.p. 151°–162°C. from benzene);

N-(tert-butyl)-2-(2-phenyl-1,3-benzodioxol-2-yl)-acetamide (m.p. 142°–144°C. from 80% alcohol);

(2-methyl-1,3-benzodioxol-2-yl)-acetamide (m.p. 114°–6°C. from benzene-hexane);

N,N-diethyl-2-(2-methyl-1,3-benzodioxol-2-yl)acetamide;

N-isopropyl-2-(2-methyl-1,3-benzodioxol-2-yl)acetamide;

3-(2-methyl-1,3-benzodioxol-2-yl)propionamide (m.p. 63°–4°C. from benzene-hexane).

EXAMPLE 12

(2-Methyl-1,3-benzodioxol-2-yl)acetohydroxamic acid.

To a solution of 2.5 g. of sodium in 75 cc. of absolute $CH_3OH$ a solution of 3.5 g. of $NH_2OH.HCl$ in 50 cc. of $CH_3OH$ is added, and, after filtration, 11 g. of ethyl 2-methyl-1,3-benzodioxol-2-yl-acetate are added to this mixture. The mixture is refluxed for 30 minutes; the methanol is removed, and the mixture is cooled and acidified with dilute HCl. The acidified mixture is extracted with ether, and the ether phase is separated, washed with $H_2O$ until it becomes neutral, and dried with $Na_2SO_4$. The product obtained after evaporation of the ether has m.p 120°–122°C. (from ethyl acetate).

(2-Phenyl-1,3-benzodioxol-2-yl)acetohydroxamic acid (m.p. 120°–21°C. from ethyl acetate can be similarly prepared).

EXAMPLE 13

(2-Phenyl-1,3-benzodioxol-2-yl)acetic acid.

a. (2-Phenyl-1,3-benzodioxol-2-yl)acetonitrile;

2.45 g. of catecholphosphotrichloride and 2.55 g. of (2-phenyl-1,3-benzodioxol-2-yl)-acetamide are carefully mixed in a distilling flask. The mixture is heated at 100°C., for 1 h. The mixture is then diluted with ether and poured onto ice. The ether phase, after being separated, is washed with $NaHCO_3$ and with $H_2O$ until it becomes neutral, and subsequently evaporated to dryness. The product melts at 111°–112°C. (from 80% alcohol).

The same product can also be obtained by treating the corresponding acetamide with $P_2O_5$.

b. 24 g. of (2-phenyl-1,3-benzodioxol-2-yl)-acetonitrile are mixed in 100 cc. of 95% ethyl alcohol. To the mixture a solution of 6.85 g. of 90% OH in 50 cc. of $H_2O$ is added. The mixture is then refluxed until evolution of $NH_3$ ceases (4 h.). The alcohol is removed under vacuum and the product is acidified by addition of dilute $H_2SO_4$. The product obtained melts at 152°–153°C. (from benzene).

EXAMPLE 14

(2-Phenyl-1,3-benzodioxol-2-yl)acetic acid.

a. 2-Phenyl-2-bromomethyl-1,3-benzodioxole. To a mixture of 40 g. of bromoacetophenone and 24 g. of pyrocatechol, heated to 90°C., 40 g. of $P_2O_5$ are added in portions. After 15 minutes, the heating is interrupted and benzene (400 cc.) is added to the mixture. The organic phase is separated, and repeatedly washed with $NaHCO_3$ and with $H_2O$ until neutral, and finally dried with $Na_2SO_4$. The dried extract is fractionated, and the desired product boils at 120°–125°C./0.4 mm.

b. To a mixture of 0.61 g. of magnesium, in chips, 10 cc. of anhydrous ether and one crystal of iodine, one cc. of a solution of 7.3 g. of 2-phenyl-2-bromoethyl-1,3-benzodioxole in 25 cc. of anhydrous ether is added. When the reaction has begun, the mixture is stirred and the rest of the mixture is then added dropwise. The mixture is then refluxed for 2 hours. After cooling $CO_2$ is bubbled into the reaction mixture for 2 hours. The mixture is then cooled with ice and hydrolysed with 25% $H_2SO_4$. The ether phase is then separated and dried with $Na_2SO_4$. After evaporation, the product obtained has the m.p. 152°–53°C. (from benzene).

EXAMPLE 15

Ethyl-3-(2-phenyl-5-chloro-1,3-benzodioxol-2-yl)-propionate.

11.7 g. of (2-phenyl-5-chloro-1,3-benzodioxol-2-yl)-acetic acid mixed with 50 cc. of anhydrous benzene are refluxed with 10 cc. of $SOCl_2$ for 3 hours. The solvent and the excess of $SOCl_2$ are removed under vacuum. The residual oil mixed with 150 cc. of anhydrous ether is added in drops to an ether solution of diazomethane, which is ice cooled to maintain the temperature under 2°–3°C. After 24 h, the ether is removed under vacuum and the residue is mixed with 100 cc. of ethanol. The mixture is heated at 50°C., and 2 g. of $Ag_2O$ are added. After 2 hours, the product is treated with animal charcoal, filtered and dried. It is then fractionated and the desired product boils at 200°–207°C./0.4 mm.

EXAMPLE 16

Ethyl spiro-(1,3-benzodioxol-2,1'-cyclopentane)-2'-carboxylate.

A mixture of 15.7 g. of ethyl cyclopentanone-2-carboxylate, 11 g. of pyrocatechol, 0.5 g. of p-toluenesulphochloride and 0.5g. of p-toluenesulphonic acid in 100 cc. of anhydrous benzene is refluxed until the theoretical amount of water no longer distils azeotropically. The mixture is washed first with dilute NaOH and then with $H_2O$ until neutral. After drying with $Na_2SO_4$ the solvent is removed under vacuum. The residual oil is fractionated, and the desired product boils at 136°–139°C./0.3 mm.

The following is prepared similarly:

Ethyl spiro-(1,3-benzodioxol-2,1'-cyclohexane)-2'-carboxylate (b.p. 137°C./0.2 mm.).

EXAMPLE 17

Ethyl(2-methyl-5-amino-1,3-benzodioxol-2-yl)acetate 16 g. of ethyl(2-methyl-5-nitro-1,3-benzodioxol-2-yl)-acetate (prepared according to G. Sloof, Rec. Trav. Chim. 547, 995 (1935)) dissolved in 300 cc. of 95% alcohol are hydrogenated at room temperature and 2 atm. of hydrogen pressure in the presence of 6 g. of Raney nickel. After the theoretical absorption of hydrogen, the mixture is filtered and evaporated to dryness. The residual oil is purified by distillation, (b.p. 190°–200°C./0.4 mm.).

The following can be prepared similarly:

(2-methyl-5-amino-1,3-benzodioxol-2-yl)acetic acid.

EXAMPLE 18

Ethyl(2-methyl-5-N,N-diethylsulphonamido-1,3-benzodioxol-2-yl)acetate.

a. To 5 g. of ethyl(2-methyl-1,3-benzodioxol-2-yl)-acetate in 25 cc. of dried chloroform, 25 cc. of chlorosulphonic acid is added at 0°C., in drops, and with stirring. After the addition, the mixture is stirred for 2 hours and then poured onto ice and extracted with ether. The organic phase, after being washed first with a solution of $Na_2CO_3$ and then with $H_2O$ until neutral, is dried with $Na_2SO_4$. The residual oil, ethyl(2-methyl-5-chlorosulphonyl-1,3-benzodioxol-2-yl)-acetate, is used without further purification for the subsequent reaction.

b. To 5 g. of ethyl(2-methyl-5-chlorosulphonyl-1,3-benzodioxol-2-yl)-acetate diluted in 50 cc. of anhydrous benzene, 2.3 g. of diethylamine are added. The mixture is refluxed for 30 minutes, and then filtered and dried. It is purified by distillation, and the desired product boils at 250°–60°C./0.4 mm.

Ethyl(2-methyl-5-sulphonamido-1,3-benzodioxol-2-yl)acetate is similarly prepared.

EXAMPLE 19

Ethyl(2-methyl-5-acetylamino-1,3-benzodioxol-2-yl)acetate.

A mixture of 4.5 g. of ethyl(2-methyl-5-amino-1,3-benzodioxol-2-yl)-acetate and 30 cc. of acetic anhydride is heated for 15 minutes at 100°C. After cooling, it is poured onto ice, and allowed to stand for 2 hours. The precipitated solid is filtered off, and crystallised from aqueous alcohol, m.p. 81°–82°C.

We claim:

1. N-(($\beta$-N',N'-diethylamino)ethyl)-2-(2-methyl-1,3-benzodioxol-2-yl)-acetamide or a pharmaceutically acceptable salt thereof.

2. N-(($\beta$-N',N'-diethylamino)ethyl)-2-(2-phenyl-1,3-benzodioxol-2-yl)-acetamide or a pharmaceutically acceptable salt thereof.

3. N-(($\beta$-N',N'-diethylamino)ethyl)-spiro-(1,3-benzodioxol-2,1'-cyclohexane)-2'carboxyamide or a pharmaceutically acceptable salt thereof.

4. N-(($\beta$-N',N'-dimethylamino)ethyl)-2-(2-methyl-1,3-benzodioxol-2-yl)-acetamide or a pharmaceutically acceptable salt thereof.

5. N-(($\beta$-N',N'-diethylamino)ethyl)-2-(2-methyl-1,3-benzodioxol-2-yl)-propionamide or a pharmaceutically acceptable salt thereof.

6. N-(($\beta$-N',N'-diethylamino)ethyl)-3-(2-methyl-1,3-benzodioxol-2-yl)-propionamide or a pharmaceutically acceptable salt thereof.

7. N-(($\beta$-N',N'-diethylamino)ethyl)-2-(2,5-dimethyl-1,3-benzodioxol-2-yl)-acetamide or a pharmaceutically acceptable salt thereof.

* * * * *